US008377471B2

(12) United States Patent
Vanquickenborne et al.

(10) Patent No.: US 8,377,471 B2
(45) Date of Patent: Feb. 19, 2013

(54) CONTAINER

(75) Inventors: Stef Vanquickenborne, Rijmenam (BE); Jan Sinnaeve, Ledeberg (BE)

(73) Assignee: Capsugel Belgium NV, Bornem (BE)

( * ) Notice: Subject to any disclaimer, the term of this patent is extended or adjusted under 35 U.S.C. 154(b) by 1548 days.

(21) Appl. No.: 11/498,402

(22) Filed: Aug. 3, 2006

(65) Prior Publication Data

US 2007/0184077 A1 Aug. 9, 2007

Related U.S. Application Data

(63) Continuation-in-part of application No. 11/485,686, filed on Jul. 13, 2006.

(60) Provisional application No. 60/706,604, filed on Aug. 9, 2005.

(51) Int. Cl.
*A61K 9/48* (2006.01)

(52) U.S. Cl. ................................ 424/454; 220/DIG. 34

(58) Field of Classification Search .................. 424/454; 220/DIG. 34

See application file for complete search history.

(56) References Cited

U.S. PATENT DOCUMENTS

| | | | | | |
|---|---|---|---|---|---|
| 2,718,980 | A | * | 9/1955 | Strom | 220/780 |
| 3,508,678 | A | * | 4/1970 | Noren et al. | 220/785 |
| 3,584,759 | A | | 6/1971 | Lorinez | |
| 3,664,495 | A | | 5/1972 | Graham et al. | |
| 3,702,653 | A | | 11/1972 | Mottin et al. | |
| 3,823,843 | A | | 7/1974 | Stephens et al. | |
| 3,927,195 | A | | 12/1975 | Messora | |
| 4,040,536 | A | | 8/1977 | Schwarz | |
| 4,196,564 | A | | 4/1980 | Bodenmann et al. | |
| 4,196,565 | A | | 4/1980 | Bodenmann et al. | |
| 4,247,006 | A | | 1/1981 | Bodenmann et al. | |
| 4,250,997 | A | | 2/1981 | Bodenmann et al. | |
| 4,281,763 | A | | 8/1981 | Pace | |
| 4,325,761 | A | | 4/1982 | Pace | |
| 4,442,941 | A | | 4/1984 | Keith | |
| 4,478,658 | A | | 10/1984 | Wittwer | |
| 4,487,327 | A | * | 12/1984 | Grayson | 220/8 |
| 4,534,467 | A | | 8/1985 | Rathbun | |
| 4,539,060 | A | | 9/1985 | Wittwer et al. | |
| 4,543,138 | A | | 9/1985 | Bollinger et al. | |
| 4,554,034 | A | | 11/1985 | Ensminger | |
| 4,576,284 | A | | 3/1986 | Wittwer et al. | |
| 4,601,896 | A | | 7/1986 | Nugent | |
| 4,609,417 | A | | 9/1986 | Smith | |
| 4,656,066 | A | | 4/1987 | Wittwer | |
| 4,667,498 | A | * | 5/1987 | Sauter | 72/108 |
| 4,724,019 | A | | 2/1988 | Brown et al. | |
| 4,792,451 | A | | 12/1988 | Kim | |
| 4,893,721 | A | * | 1/1990 | Bodenmann et al. | 220/8 |
| 5,074,426 | A | | 12/1991 | Goodhart et al. | |
| 5,632,971 | A | | 5/1997 | Yang | |
| 5,769,267 | A | * | 6/1998 | Duynslager et al. | 220/691 |
| 5,770,224 | A | | 6/1998 | Rashid et al. | |

FOREIGN PATENT DOCUMENTS

| | | | | |
|---|---|---|---|---|
| EP | 180543 | A2 | * | 5/1986 |
| EP | 1072245 | A1 | * | 1/2001 |
| GB | 2172569 | A | | 9/1986 |
| GB | 2172570 | A | | 9/1986 |
| JP | 54-23117 | A | | 2/1979 |

* cited by examiner

*Primary Examiner* — Gina C Justice
*Assistant Examiner* — Michael B Pallay
(74) *Attorney, Agent, or Firm* — Finnegan, Henderson, Farabow, Garrett & Dunner, LLP

(57) ABSTRACT

A container and more specifically a container such as a capsule used to deliver dosages of pharmaceuticals, medicines, vitamins, etc. to an individual is discussed. In one embodiment, the invention includes a container comprising: a cap; a body slidably engagable inside the cap; and a fluid gap positioned between the cap and the body adjacent an end of the cap, wherein a first channel of the cap and a first channel of the body form a snap fit joint and a second channel of the cap and a second channel of the body form a fluid stop joint whereby a sealing fluid is substantially restricted to the fluid gap by the fluid stop joint.

34 Claims, 14 Drawing Sheets

FIG. 3A
FIG. 3B
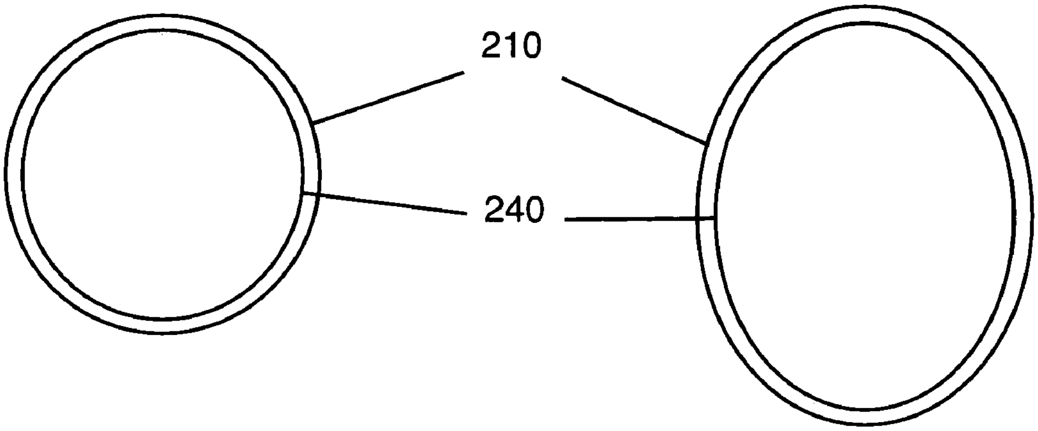
FIG. 3C
FIG. 3D
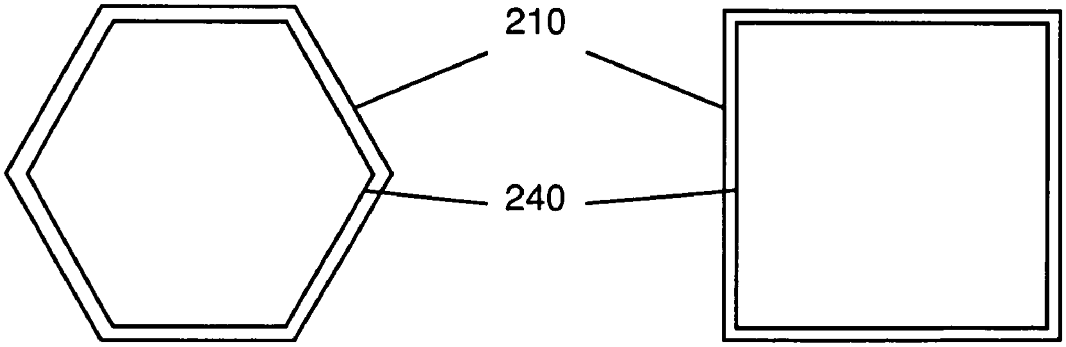

CONTAINER

CROSS-REFERENCE TO RELATED APPLICATIONS

This application claims the benefit of co-pending U.S. application Ser. No. 11/485,686, filed Jul. 13, 2006, as a continuation-in-part application and also claims the benefit of U.S. Provisional Patent Application No. 60/706,604, filed 9 Aug. 2005, which are hereby incorporated herein.

BACKGROUND OF THE INVENTION

1. Technical Field

The invention relates generally to a container and more specifically to a container such as a capsule used to deliver dosages of pharmaceuticals, medicines, vitamins, etc. to an individual.

2. Related Art

Standard containers for pharmaceuticals or other powdered, granular, or liquid substances, so-called telescope-type capsules, include a tubular-shaped or cylindrically-shaped first part, namely the cap part, which is closed on one end and open on the other end. A tightly fitting second part of similar shape, but of smaller diameter, can be telescopically inserted into the cap part, the second part being referred to as the main part or body part. FIG. 1 shows an illustrative conventional capsule 100 including a cap 110 and a body 140. Cap 110 includes an open end 112 and a closed end 114. Similarly, body 140 includes an open end 142 and a closed end 144. Open end 142 of body 140 is of a slightly smaller diameter than open end 112 of cap 110 such that body 140 may be partially inserted into cap 110. A separation of cap 110 and body 140 is prevented by friction and/or various modifications of an exterior surface of body 140 and/or an opposed inner surface of cap 110. For example, U.S. Pat. No. 5,769,267 to Duynslager et al., which is hereby incorporated by reference, discloses a two-piece telescoping capsule having corresponding connection units on the cap part and body as well as protrusions on an inner surface of the cap part to increase friction between the cap part and the body.

Usually, the containers are supplied to a filling apparatus in a “prelock” condition in which the body part is telescoped only partially into the cap. The two parts are separated in the filling machine and then fully closed after the filling operation.

In addition to various locking mechanisms intended to secure the various parts of a multi-part capsule after filling, the parts may alternatively or additionally be sealed by various methods. Generally, such sealing includes the spraying with a liquid or dipping of the capsule parts in a liquid. Such liquid may itself provide adhesive and/or sealing properties. Alternatively, such liquid may result in the partial dissolution or disintegration of portions of the capsule parts, whereby the capsule parts are fused or sealed upon evaporation of the liquid. Illustrative liquid sealing methods and solutions are disclosed in U.S. Pat. No. 4,893,721 to Bodenmann et al., which is hereby incorporated by reference. The particular liquid chosen will depend, in part, upon the composition of the capsule parts, but may include, for example, water or an alcohol.

Capsules may be constructed from a variety of film-forming agents such as gelatin, hydroxypropylmethylcellulose (HPMC), pullulan, etc. A number of defects have been observed in known devices, particularly deformations and microcracks in capsule walls. Deformations may result from a thinning and/or weakening of a capsule wall due to an excess of sealing fluid, which necessarily at least partially dissolves or disintegrates a material of the capsule wall.

Microcracks generally take the form of small breaks or discontinuities and almost always appear near a locking structure cap, i.e., portions of the cap and body providing a friction fit to prevent opening of the capsule. Microcracks result from stresses upon the capsule parts combined with a locally low loss on drying (LOD), i.e., low moisture content, and thus brittleness. Stresses may result, for example, from an internal capsule pressure, e.g., from the closing and/or heating of the capsule, or stresses placed upon the capsule parts themselves due to the force required to insert the capsule body into the capsule cap. The locally low LOD or brittleness may result, for example, from the presence of an alcohol vapor, which acts as a dehumidifier, in a gap between the cap and the body or from the drying of the capsule material, also attributable to an alcohol in the sealing fluid.

It has been observed that pullulan is particularly susceptible to these defects. Pullulan capsules experience higher than normal rates of failure after a sealing process, due, at least in part, to the fact that pullulan dissolves in room temperature water. Gelatin forms a phase intermediate between a solid and a liquid upon application of water, wherein the chain structure of the gelatin remains intact. In contrast, upon the application of water, pullulan transitions from a solid to a liquid. As a result, the strength of pullulan is lost locally near the sealing area. In this case, deformations may be common, resulting in the bending, swelling, or rupturing of capsules. Examples of failure include improper sealing, deformation, etc. As a result, current capsule designs are not well suited to allow for the liquid sealing of a pullulan-based multi-piece capsule.

There is, therefore, a need in the art for a multi-piece capsule design that can be sealed, such as with a conventional alcohol/water spray, and is not susceptible to deformation or failure of the capsule due to a liquid sealing process.

SUMMARY OF THE INVENTION

A container and more specifically a container such as a capsule used to deliver dosages of pharmaceuticals, medicines, vitamins, etc. to an individual is disclosed. In one embodiment, the invention includes a container comprising: a cap; a body slidably engagable inside the cap; and a fluid gap positioned between the cap and the body adjacent an end of the cap, wherein a first channel of the cap and a first channel of the body form a snap fit joint and a second channel of the cap and a second channel of the body form a fluid stop joint whereby a sealing fluid is substantially restricted to the fluid gap by the fluid stop joint.

A first aspect of the invention provides a container comprising: a cap; a body slidably engagable inside the cap; and a fluid gap positioned between the cap and the body adjacent an end of the cap, wherein a first channel of the cap and a first channel of the body form a snap fit joint characterized as free of contact with a sealing fluid and a second channel of the cap and a second channel of the body form a fluid stop joint whereby a sealing fluid is substantially restricted to the fluid gap by the fluid stop joint.

A second aspect of the invention provides a container comprising: a cap having a first channel and a second channel; a body slidably engagable inside the cap, the body having a first channel engagable with the first channel of the cap in a first position and the second channel of the cap in a second position, a second channel engagable with the second channel of the cap in the second position, and a third channel forming an entry gap adjacent an open end of the cap; and a fluid gap between the cap and the body adjacent an end of the cap.

A third aspect of the invention provides a container comprising: a cap having a first channel and a second channel; a body slidably engagable inside the cap, the body having a first channel engagable with the first channel of the cap in a first position and the second channel of the cap in a second position, a second channel engagable with the second channel of the cap in the second position, and a third channel forming an entry gap adjacent an open end of the cap; a fluid gap positioned between the cap and the body adjacent an end of the cap; and a pressure release channel, wherein the first channel of the cap and the first channel of the body form a snap fit joint, the second channel of the cap and the second channel of the body form a fluid stop joint for substantially restricting sealing fluid to the fluid gap, and the pressure release channel is located substantially within the snap fit joint.

A fourth aspect of the invention provides a container comprising: a cap having a first channel and a second channel; a body slidably engagable inside the cap, the body having a first channel engagable with the second channel of the cap and a second channel forming an entry gap adjacent an open end of the cap; and a fluid gap between the cap and the body adjacent an end of the cap, wherein the second channel of the cap and a portion of the body between an open end of the body and the first channel of the body form a pre-lock joint in a first position and the second channel of the cap and the first channel of the body form a fluid stop joint for substantially restricting a sealing fluid to the fluid gap in a second position.

A fifth aspect of the invention provides a method of sealing a multi-part container comprising: providing a container having: a cap; a body slidably engagable inside the cap; and a fluid gap positioned between the cap and the body adjacent an end of the cap; closing the container such that a first channel of the cap and a first channel of the body are in contact and a second channel of the cap and a second channel of the body are in contact; applying a sealing fluid to the fluid gap; and drying the container.

The illustrative aspects of the present invention are designed to solve the problems herein described and other problems not discussed, which are discoverable by a skilled artisan.

BRIEF DESCRIPTION OF THE DRAWINGS

The embodiments of this invention will be described in detail, with reference to the following figures, which are not drawn to scale, wherein like designations denote like elements, and wherein:

FIGS. 3A-D show cross-sectional views of various embodiments of the invention.

DETAILED DESCRIPTION

Figure 2:
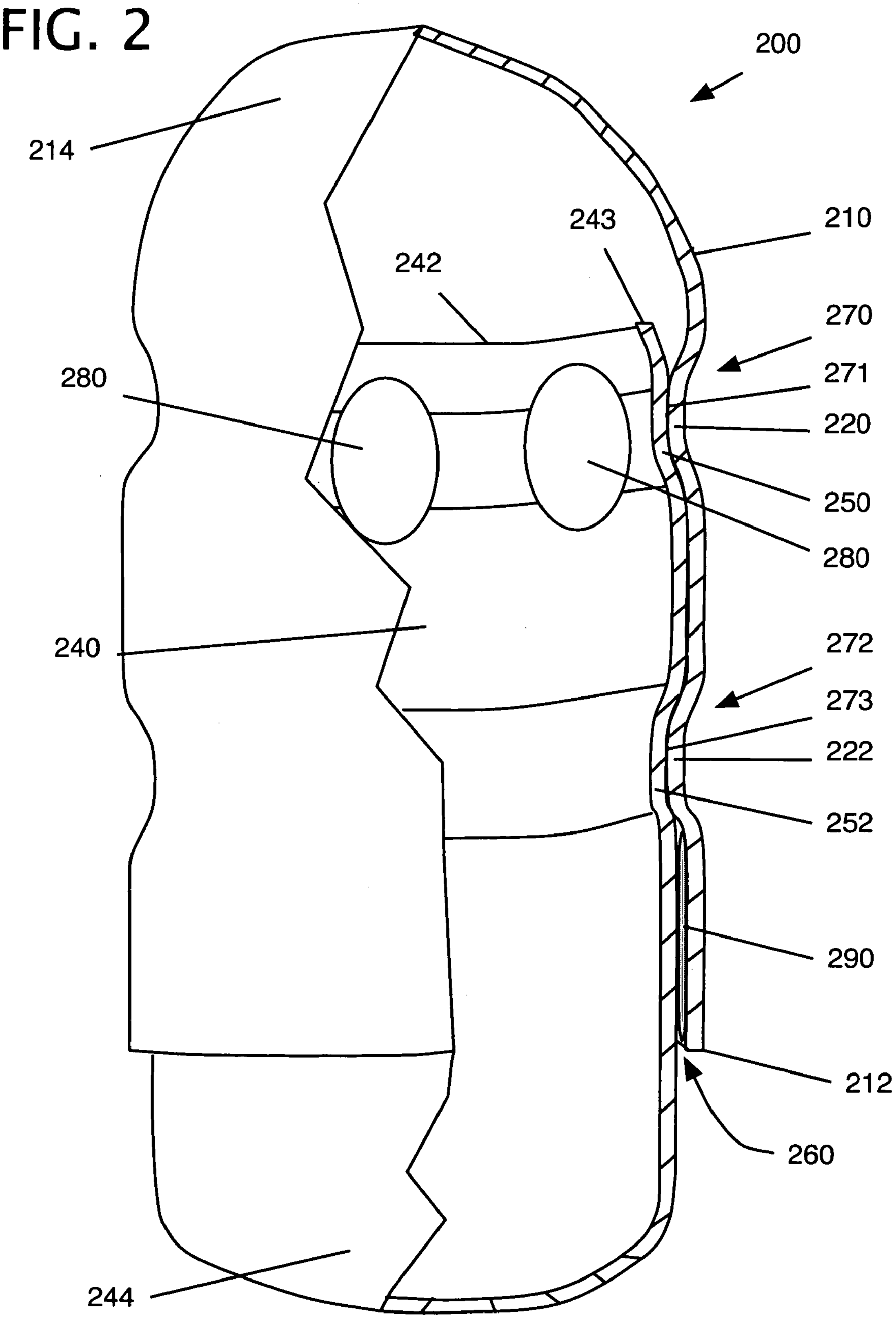
FIG. 2 shows a partial cross-sectional view of an embodiment of the invention.

Referring to FIG. 2, a first illustrative embodiment of the present invention is shown. Container 200 comprises cap 210 and body 240. Each of cap 210 and body 240 includes an open end 212 and 242, respectively. Open end 212, 242 may be of any number of cross-sectional shapes, including, for example, circular, ovoid, hexagonal, or square. In one preferred embodiment, each open end 212, 242 is circular in cross-section. Open end 242 is of a slightly smaller diameter than open end 212, such that body 240 may be at least partially inserted into cap 210. Optionally, open end 242 may include an inward taper 243 to facilitate insertion of body 240 into cap 210, although such a feature is not essential.

Opposite open end 212, 242, each of cap 210 and body 240 includes a closed end 214, 244. While somewhat dependent upon the cross-sectional shape of the open end, a closed end may be of any number of shapes, including, for example, hemispherical or pyrimidal. The closed ends of cap 210 and body 240 may have the same or different shapes. In one preferred embodiment, each closed end is hemispherical in shape.

The cross-sectional shapes of cap 210 and body 240 at points between their open and closed ends may be different than the cross-sectional shapes at either their open ends or closed ends. That is, the cross-sectional shape of cap 210 and/or body 240 may change between their open ends and closed ends. However, since body 240 is ultimately to be at least partially inserted into cap 210, no cross-sectional shape of either should impede such insertion.

In order to prevent the separation of cap 210 and body 240 after capsule 200 is assembled, container 200 includes a snap fit joint 270 comprising corresponding channels 220 and 250 on cap 210 and body 240, respectively. By "corresponding," it is meant that channels 220, 250 are of compatible shape and size such that one may rest atop the other. However, channels 220, 250 need not be identical in shape or size. For example, channel 220 may have a V-shape while channel 250 may have a U-shape. Channels 220, 250 are each preferably continuous along a circumference of cap 210 and body 240, respectively, although one or both may also be discontinuous or segmented. Snap fit joint 270 preferably includes a radially-oriented interference gap 271 between cap 210 and body 240 of between about 20 μm and about 60 μm, and more preferably about 40 μm. Snap fit joint 270 preferably has a height (i.e., a length along an axis of container 200) of between about ⅙ and about ½, and more preferably between about ⅕ and about ⅓ the height of container 200 when fully closed. For example, for a size 2 container having a closed height of about 18 mm, a height of snap fit joint 272 would be between about 1 mm and about 5 mm, and more preferably between about 1.2 mm and about 2 mm. Other sizes may also be possible.

Figure 1:
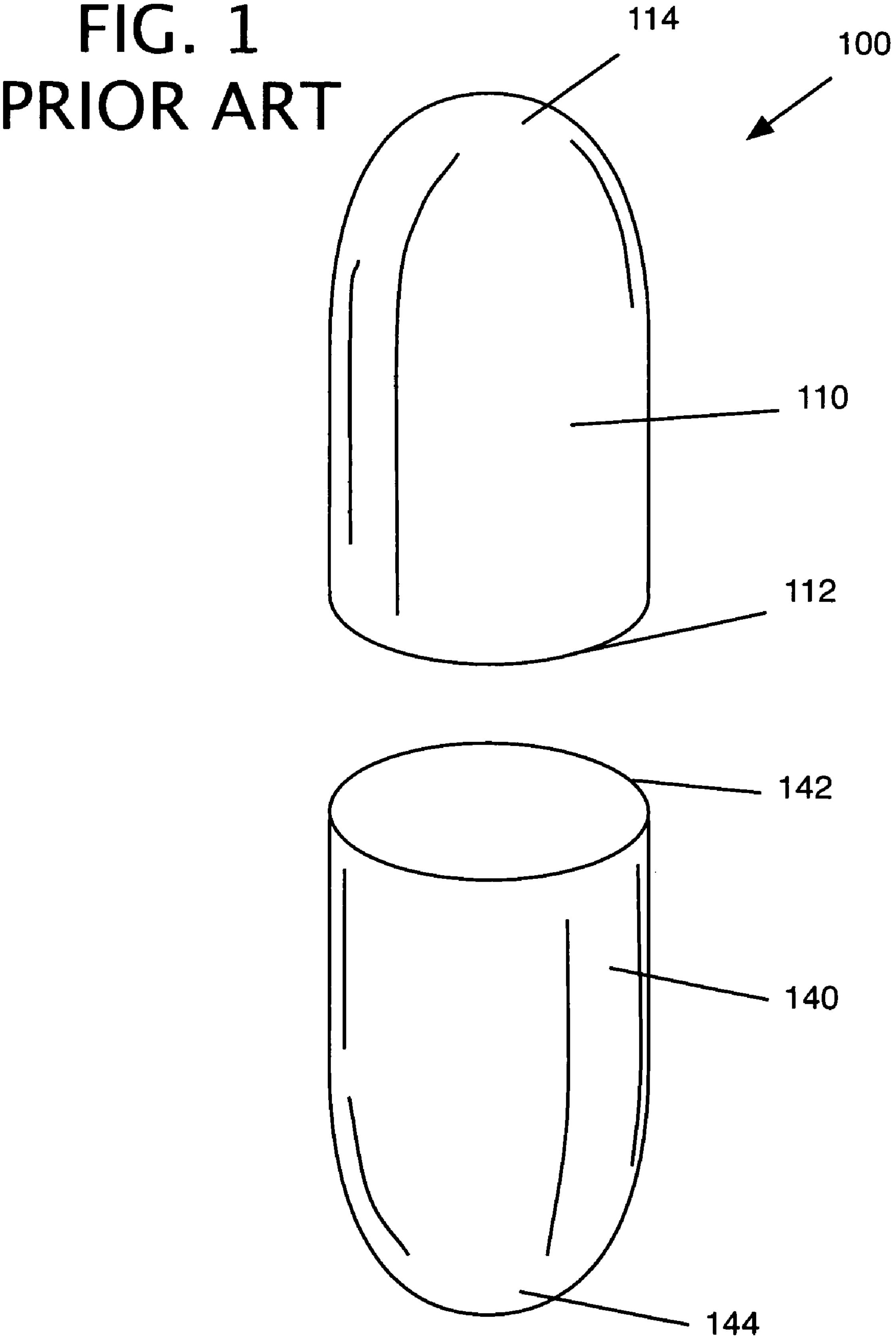
FIG. 1 PRIOR ART
FIG. 1 shows a conventional two-piece capsule device.

A small amount of sealing fluid 290 may enter fluid gap 260, resulting in the partial dissolution or disintegration of a portion of cap 210 and body 240 and then a fusing of cap 210 and body 240 upon evaporation and/or removal of sealing fluid 290. As such, the fusing of cap 210 and body 240 provides a seal that is tamperproof or tamper evident, i.e., opening container 200 after such fusing requires destruction of the seal. Fluid gap 260 preferably has a width, i.e., between an internal surface of cap 210 and an external surface of body 240, between about 20 μm and about 120 μm, and more preferably about 40 μm. Fluid gap 260 preferably has a height (i.e., a length along an axis of container 200) of between about 1/10 and about 1/3, and more preferably between about 1/8 and about 2/9 a height of container 200 when fully closed. For example, for a size 2 container 200 having a closed height of about 18 mm, fluid gap 260 preferably has a height between about 2 mm and about 5 mm, and more preferably about 3 mm and about 4 mm. Other sizes may also be possible. The volume of fluid gap 260 is smaller than analogous features of known devices. This smaller volume results in less sealing fluid 290 between cap 210 and body 240 and therefore less deformation of either cap 210 or body 240 following the sealing of container 200. Fluid gap 260 is preferably substantially uniform in width, i.e., cap 210 is preferably equally spaced from body 240 along a length of fluid gap 260. The uniformity of fluid gap 260 thus results in less sealing fluid 290 at the open end 212 of cap 210, as compared to the conical-shaped gaps of known devices, wherein the gap is greater nearer open end 112 (FIG. 1) of cap 110 (FIG. 1).

In order to prevent excess sealing fluid 290 from entering far into fluid gap 260 between cap 210 and body 240 and weakening one or both of cap 210 and body 240, container 200 may optionally further include a fluid stop joint 272 comprising corresponding channels 222 and 252 on cap 210 and body 240, respectively. Channels 222, 252 are each preferably continuous along a circumference of cap 210 and body 240, respectively, although one or both may also be discontinuous or segmented. Fluid stop joint 272 preferably includes a gap 273 between cap 210 and body 240 of between about −20 μm and about +10 μm, and more preferably about 0 μm. Fluid stop joint 272 preferably has a height (i.e., a length along an axis of container 200) of between about 1/9 and about 1/6, more preferably between about 1/26 and about 1/20, and most preferably about 1/21 a height of container 200 when fully closed. For example, for a size 2 container 200 having a height of about 18 mm when fully closed, fluid stop joint 272 would have a height between about 0.2 mm and about 3.5 mm, more preferably between about 0.7 mm and about 0.9 mm, and most preferably about 0.86 mm. Other sizes may also be possible.

In a particularly preferred embodiment, container 200 includes both snap fit joint 270 and fluid stop joint 272. Such an arrangement uncouples the stress and brittleness (due to locally low LOD) defects of known devices. That is, rather than stress and brittleness affecting the same portion of container 200, a container 200 of this embodiment that includes both a snap fit joint 270 and a fluid stop joint 272 restricts stresses to snap fit joint 270 and eliminates or reduces brittleness by restricting sealing fluid 290 (and therefore alcohol vapors) to fluid gap 260. In addition, with such an arrangement, fluid stop joint 272 inhibits or stops the capillary action of sealing fluid 290, resulting in less sealing fluid 290 between cap 210 and body 240 and faster, more efficient drying of container 200.

Container 200 may optionally further include one or more pressure release channels 280 on body 240 for allowing the escape of gas within container 200 upon the insertion of body 240 into cap 210. In one embodiment, pressure release channel 280 comprises a depression within a surface of body 240. Pressure release channel 280 may have any number of cross-sectional shapes, including, for example, ovoid and circular. In one embodiment, pressure release channel 280 is preferably ovoid in cross-section. Preferably, pressure release channel 280 is located substantially within the area of snap fit joint 270 and is not located within fluid stop joint 272. Such an arrangement provides a particular advantage over known capsules when used in conjunction with snap fit joint 270 and fluid stop joint 272. In known devices, pressure release channels permit gas to escape from a capsule during the drying process, wherein the capsule is heated. The escape of gas during this step causes the formation of gas channels within the sealing area, which compromise the integrity of the seal, permitting the leaking of capsule contents and/or failure of the seal. By restricting pressure release channel 280 to the area of snap fit joint 270 and including fluid stop joint 272, gas is allowed to escape from within container 200 as it is closed but is prevented from escaping by fluid stop joint 272 once container 200 is fully closed. As such, gas does not escape from container 200 during the drying process and gas channels (not shown) do not form in the sealing area. The result is an uninterrupted seal providing increased strength and integrity.

In addition, it has been found that deformation of body 240 and/or cap 210 may be prevented or reduced by utilizing a body 240 and/or cap 210 of increased thickness. Known containers typically include caps and bodies having wall thicknesses of approximately 100 μm. Utilizing a cap and/or body having a wall thickness of approximately 130 μm has been shown to significantly decrease container deformation.

FIGS. 3A-D show cross-sectional views of various alternative embodiments of the invention having different cross-sectional shapes. The shapes of both cap 210 and body 240 are circular in FIG. 3A, ovoid in FIG. 3B, hexagonal in FIG. 3C, and square in FIG. 3D. It should be noted, of course, that cap 210 and body 240 may have different cross-sectional-shapes, provided that the different shapes do not impede the insertion of body 240 into cap 210.

Figure 4:
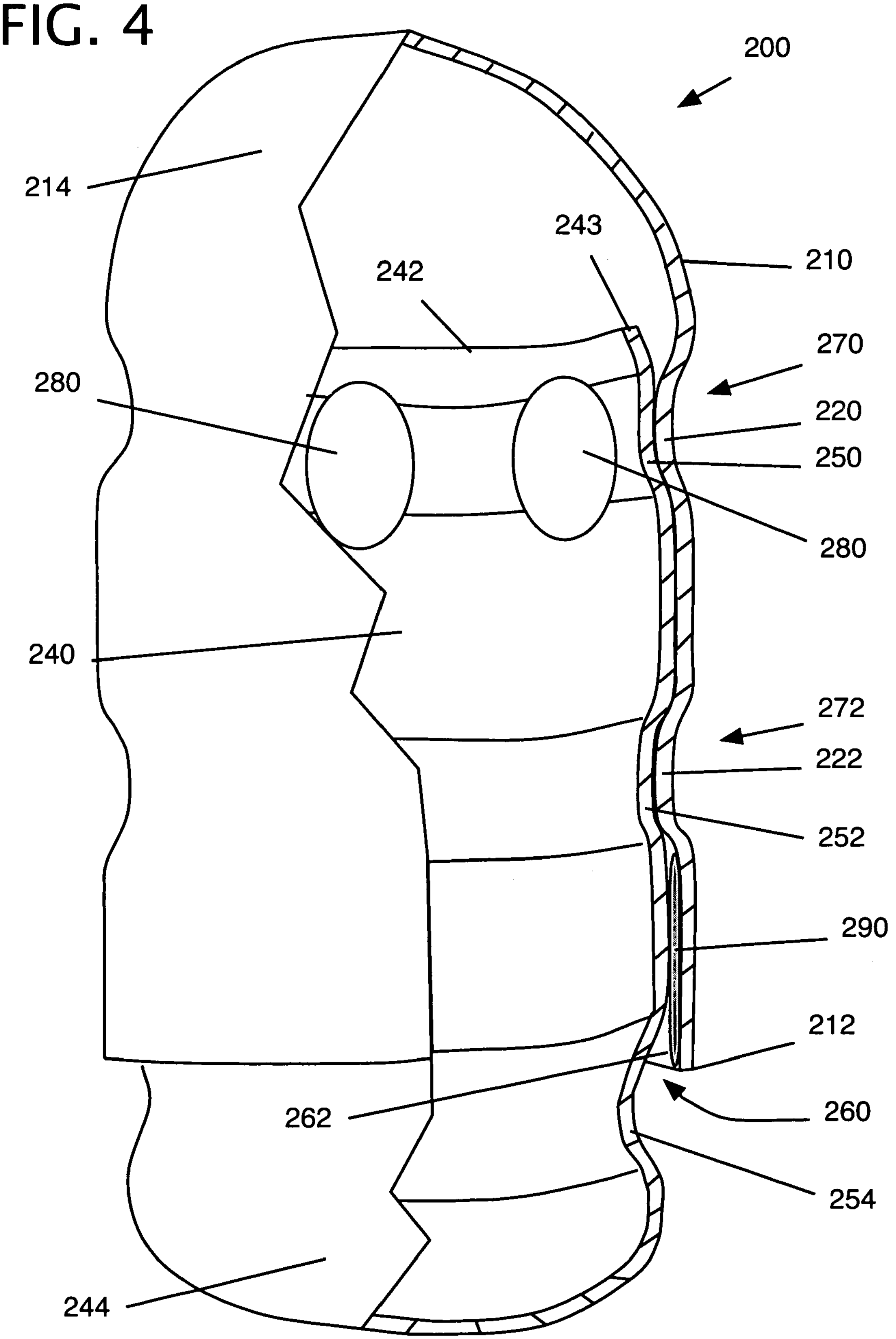
FIG. 4 shows a partial cross-sectional view of an alternative embodiment of the invention.

Referring now to FIG. 4, an alternative embodiment of the present invention is shown, wherein container 200 further includes an additional channel 254 on body 240. Additional channel 254 may have dimensions similar to those of channels 220, 250 or channels 222, 252 and is preferably located adjacent open end 212 of cap 210. Such location of additional channel 254 results in an entry gap 262 between body 240 and open end 212 of cap 210. Entry gap 262 preferably has a width (i.e., a space between body 240 and cap 210) between about 90 μm and about 200 μm, more preferably between about 110 μm and 150 μm, and most preferably about 140 μm. The inclusion of additional channel 254 provides at least three advantages. First, entry gap 262 improves the capillary action of sealing fluid 290, drawing sealing fluid 290 into fluid gap 260. Second, entry gap 262 enables better removal of excess sealing fluid 290, particularly when suction is used. Third, upon heating container 200, sealing fluid 290 is forced out of fluid gap 260 and retained within entry gap 262 rather than forming a droplet along an edge of open end 212, as is common with known devices. The formation of such a droplet contributes to capsule deformation in known devices.

Figure 5:
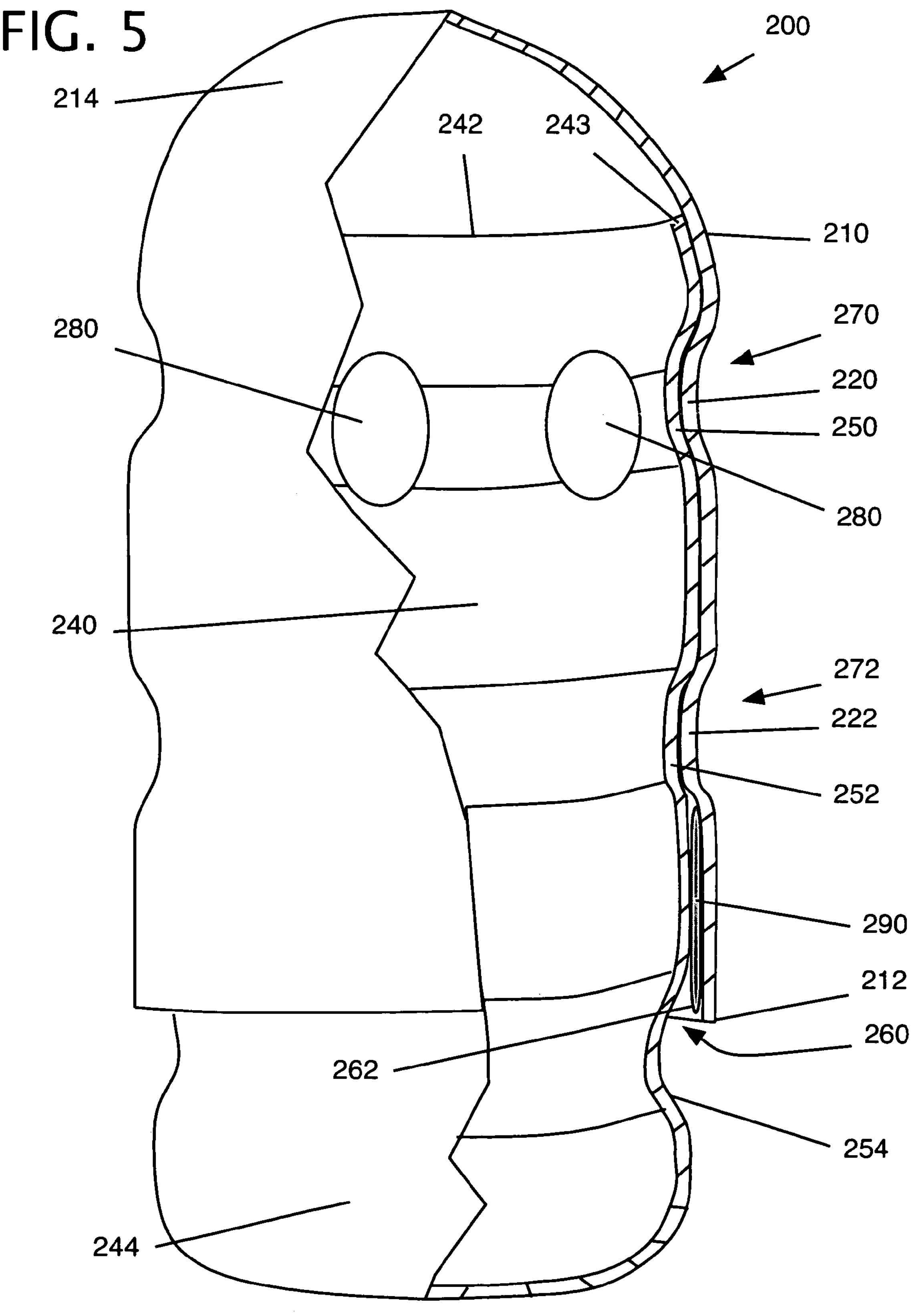
FIG. 5 shows a partial cross-sectional view of a second alternative embodiment of the invention.

FIG. 5 shows yet another alternative embodiment of a container 200 of the present invention, wherein open end 242 of body 240 is elongated such that open end 242 contacts an inner surface of cap 210 upon complete insertion of body 240 into cap 210. Open end 242 may still include inward taper 243. Elongated open end 242 provides a number of advantages over known designs. First, the formation of gas channels in sealing fluid 290, caused by the escape of gas from inside container 200 upon heating, is reduced or prevented. Second, internal pressure is substantially reduced following closing of container 200.

Figure 6A:
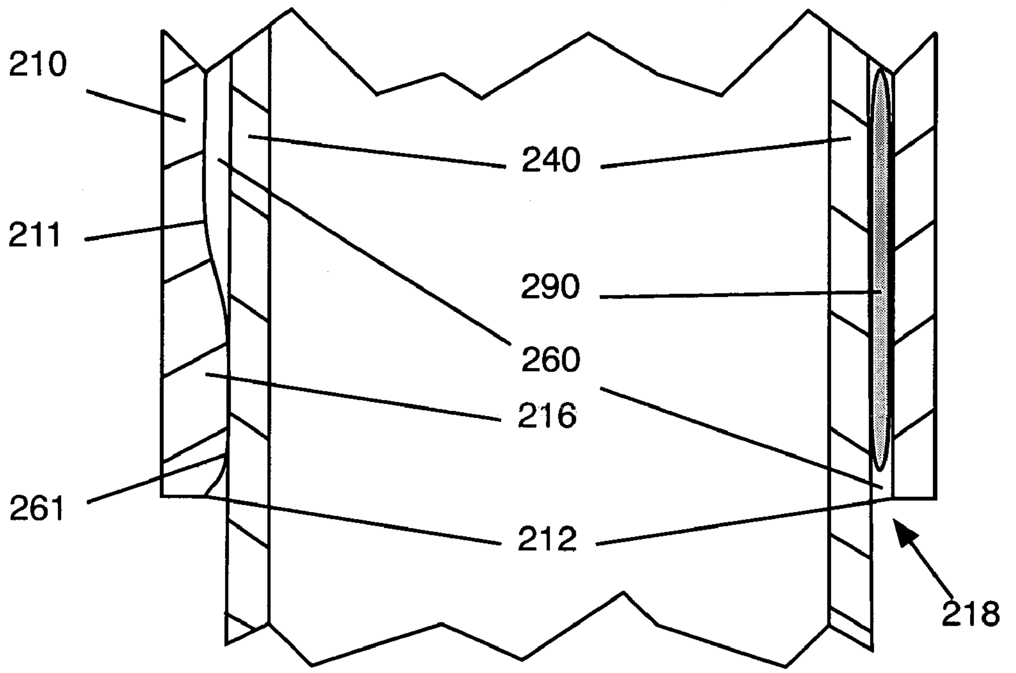
FIGS. 6A-C show cross-sectional views of third and fourth alternative embodiments of the invention.
Figure 6B:
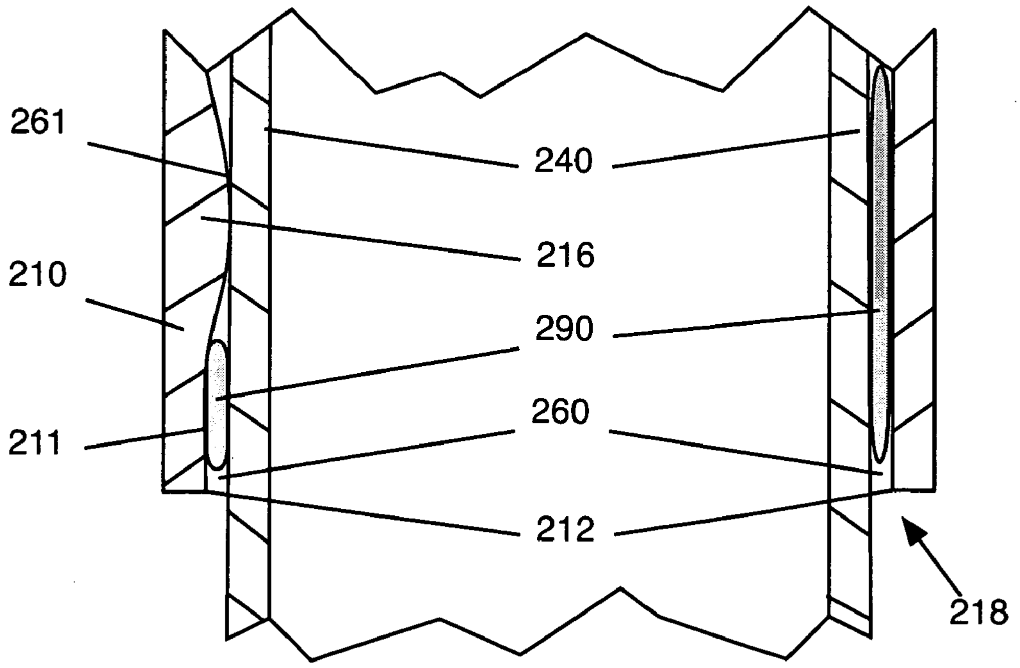

Referring now to FIGS. 6A-B, two additional alternative embodiments of a container 200 of the present invention are shown in partial cross-section. In FIG. 6A, a pillar 216 has been included on an inner surface 211 of cap 210 near open end 212. Such pillars 216 are preferably not-continuous along inner surface 211 of cap 210, but rather are located periodically along inner surface 211. Such an arrangement results in "pillared areas," as on the left side of FIG. 6A and capillary channels 218 as on the right side of FIG. 6A. Pillar 216 significantly reduces a gap 261 between cap 210 and body 240 and effectively restricts fluid gap 260 to a location further from open end 212. As noted above, fluid gap 260 preferably has a width between about 20 μm and about 120 μm, and more preferably about 40 μm. However, pillar 216 preferably changes this width to between an interference of about 30 μm and a gap of about 5 μm, and preferably to an interference of about 25 μm. The inclusion of one or more such pillars provides a number of benefits over known designs. First, pillars 216 result in less total sealing fluid 290 at open end 212, resulting in less dissolution or disintegration and therefore less deformation at open end 212. Second, where pillars 216 are located, little or no sealing fluid 290 is present at open end 212. Third, pillars 216 increase the strength of cap 210, specifically, and container 200, generally, in an area that is typically the weakest location in known designs. Fourth, the capillary channels 218 formed between pillars 216 enhance the capillary action of sealing fluid 290, drawing it further into fluid gap 260.

In FIG. 6B, pillar(s) 216 is/are located further inwardly from open end 212. Such an arrangement provides the increased strength noted above while permitting more sealing fluid 290 immediately beneath open end 212 than the embodiment in FIG. 6A. Such an arrangement may be beneficial, for example, where a stronger seal is required at open end 212. Pillars 216 may similarly be located elsewhere along an inner surface of cap 210 or an exterior surface of body 240 where increased strength, increased friction, and/or reduced sealing fluid are desirable, such as within fluid stop joint 272 (FIGS. 2-4).

Figure 6C:
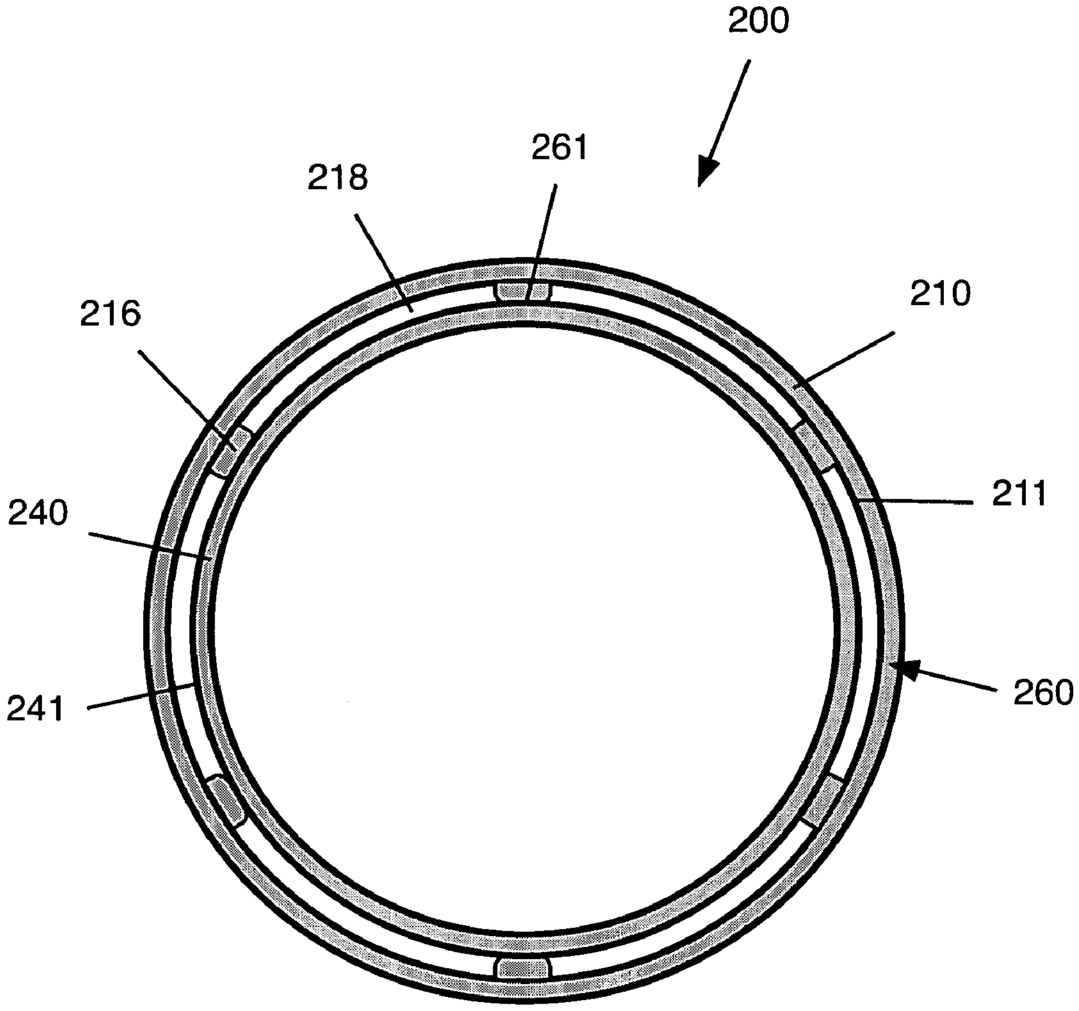

FIG. 6C shows a cross-sectional view of a particularly preferred embodiment, wherein container 200 includes a plurality of evenly-spaced pillars 216 on the inner surface 211 of cap 210, forming a plurality of evenly-spaced capillary channels 218. Most preferably, container 200 includes six evenly-spaced pillars 216, as shown. Gap 261 between each pillar 216 and body 240 is significantly reduced as compared to fluid gap 260. It should be recognized that one or more pillars 216 may similarly be located on an exterior surface 241 of body 240.

Figure 7:
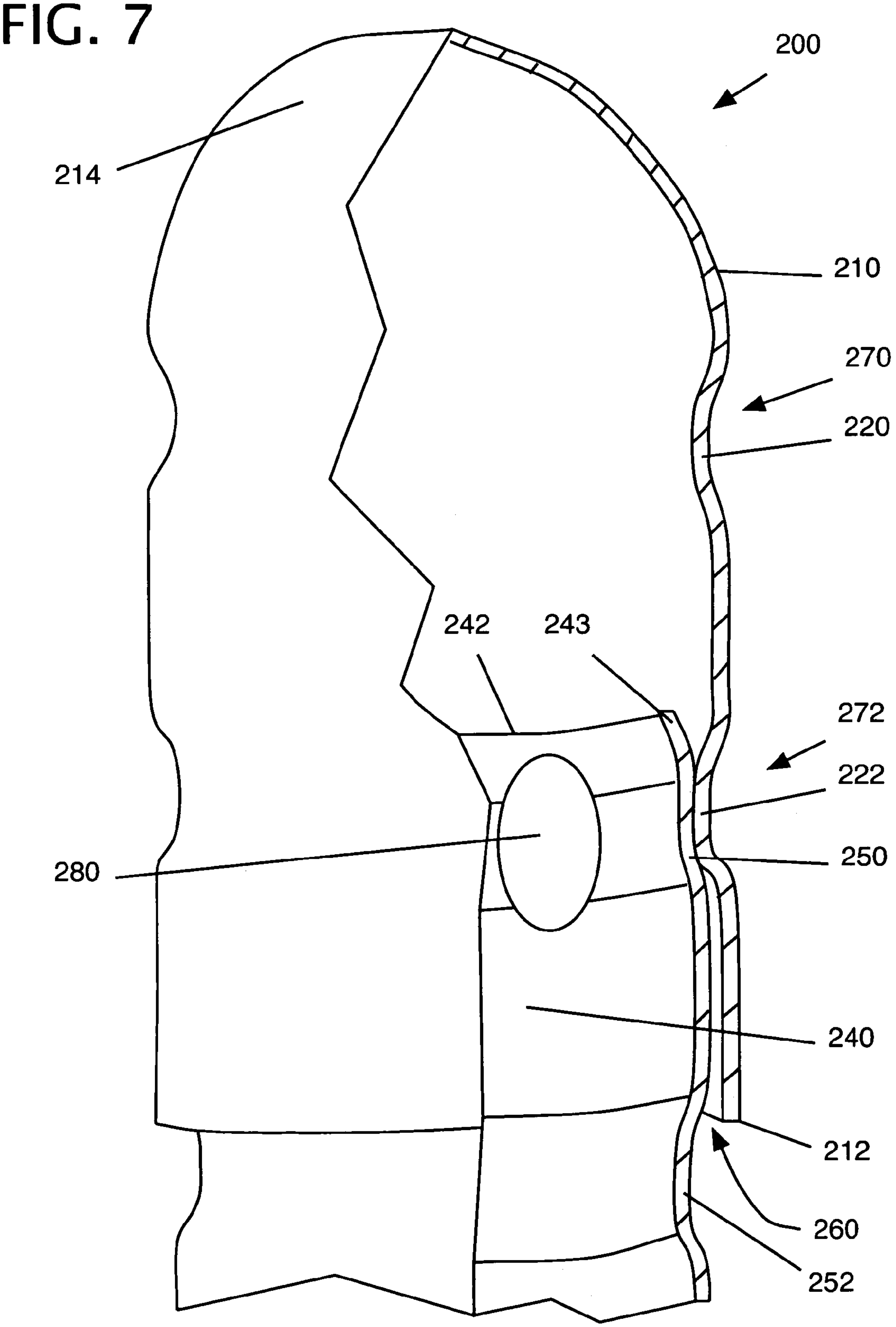
FIG. 7 shows a partial cross-sectional view of an embodiment of the invention in a prelock position.

As noted above, capsules are often supplied to a filling apparatus in a prelock condition in which the body part is telescoped only partially into the cap. FIG. 7 shows an embodiment of the present invention in such a prelock condition. Specifically, body 240 is telescopically inserted into cap 210 to the point at which channel 250 of body 240, which corresponds to channel 220 of cap 210 when container 200 is fully closed, contacts channel 222 of cap 210. That is, when inserted to the prelock position, the channel of body 240 that ultimately makes up part of snap fit joint 270 is instead inserted only as far as channel 222, the cap 210 component of fluid stop joint 272. Other prelock positions are possible, of course. For example, body 240 may be inserted into cap 210 such that channel 222 of cap 210 contacts an exterior surface (rather than channel 250) of body 240.

In such an embodiment, i.e., one that includes both a snap fit joint 270 and a fluid stop joint 272, the force necessary to disassociate cap 210 and body 240 from the prelock position may be reduced compared to known devices. This decrease in required force is attributable, in part, to the uncoupling of the stress and fluid stop functions noted above. In other words, while known devices typically utilize a single joint to both secure the cap and body and limit the egress of a sealing fluid, those functions are separate in an embodiment of the present invention having both a snap fit joint 270 and a fluid stop joint 272. As a result, the dimensions of channels making up snap fit joint 270 and fluid stop joint 272 (i.e., 220, 250 and 222, 252, respectively) may be adjusted such that an interaction of channels 222 and 250, as shown in FIG. 7, is a more loose connection than that resulting from the interaction of channels 220 and 250 and/or channels 222 and 252, as shown in FIGS. 2-4. The result, in a particularly preferred embodiment, is a container 200 with a lower prelock strength, as compared to known devices.

Figure 8A:
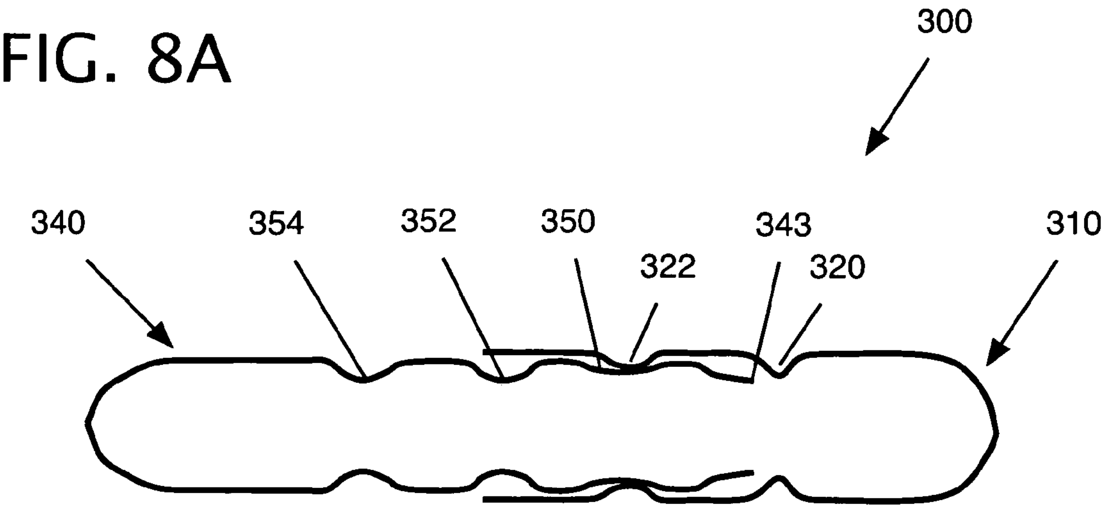
FIGS. 8A-B show cross-sectional side views of an alternative embodiment of the invention in prelock and closed positions, respectively.
Figure 8B:
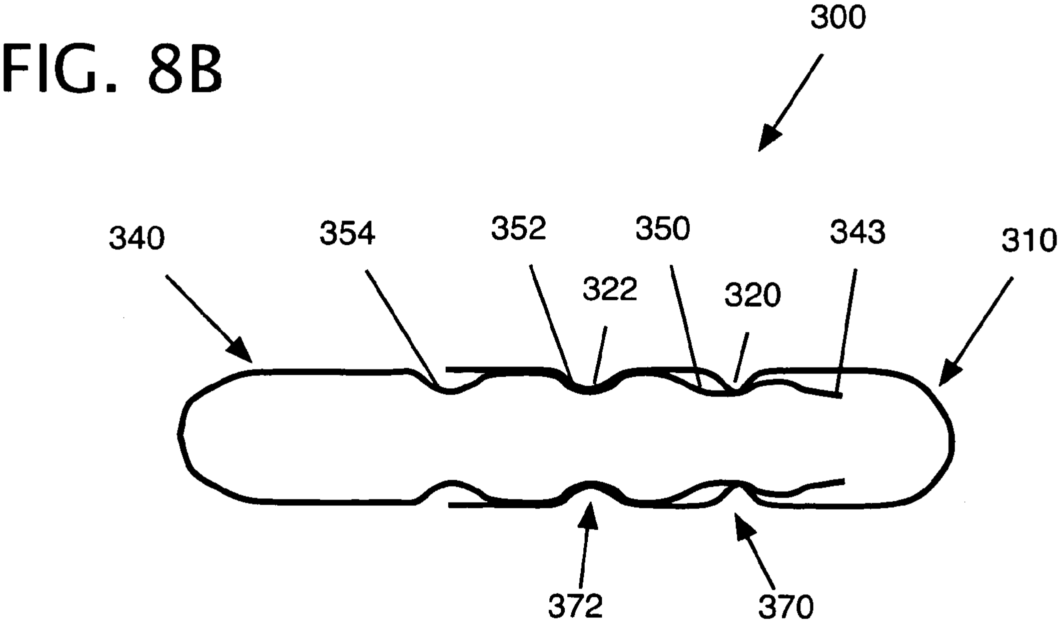

Prelock strength may similarly be lowered using any of a number of cap and body arrangements according to the invention. For example, FIGS. 8A-B show cross-sectional side views of a capsule 300 according to an alternative embodiment of the invention in a prelock and closed configuration, respectively. In FIGS. 8A-B, body 340 is shown having three channels: first channel 350, second channel 352, and third channel 354, similar to the arrangement shown in FIGS. 4-5. However, first channel 350 is both higher and shallower than shown in FIGS. 4-5. Cap 310 includes a first channel 320 and second channel 322. As shown in FIGS. 8A-B, first channel 320 of cap 310 is substantially triangular in cross-section, although this is not essential.

The increased height and decreased depth of first channel 350 of body 340 results in a looser connection between first channel 350 of body 340 and second channel 322 of cap 310 when in a prelock position, such as that shown in FIG. 8A. More specifically, an interference between body 340 and second channel 322 of cap 310 is between about −20 μm and about 50 μm, preferably between about −10 μm and 30 μm, and most preferably about 19 μm. Accordingly, a force required to remove cap 310 from body 340, when in a prelock position such as that shown in FIG. 8A, is preferably between about 5 grams and about 55 grams, preferably between about 5 grams and about 40 grams, and most preferably between about 10 grams and about 30 grams (as an average from a measurement of 10 parts).

In FIG. 8B, capsule 300 is shown in a closed position, wherein first channel 320 of cap 310 and first channel 350 of body 340 form a snap fit joint 370 and second channel 322 of cap 310 and second channel 352 of body 340 form a fluid stop joint 372. As in other embodiments described above, snap fit joint 370 includes an interference between cap 310 and body 340 of between about −20 μm and about 60 μm, and more preferably about 40 μm.

Figure 9A:
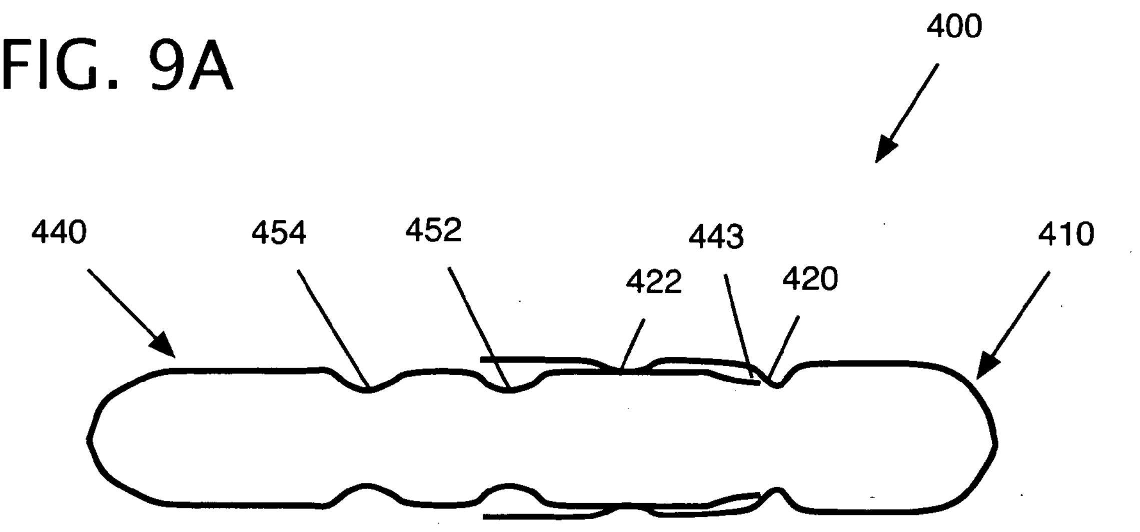
FIGS. 9A-B show cross-sectional side views of an alternative embodiment of the invention in prelock and closed positions, respectively.
Figure 9B:
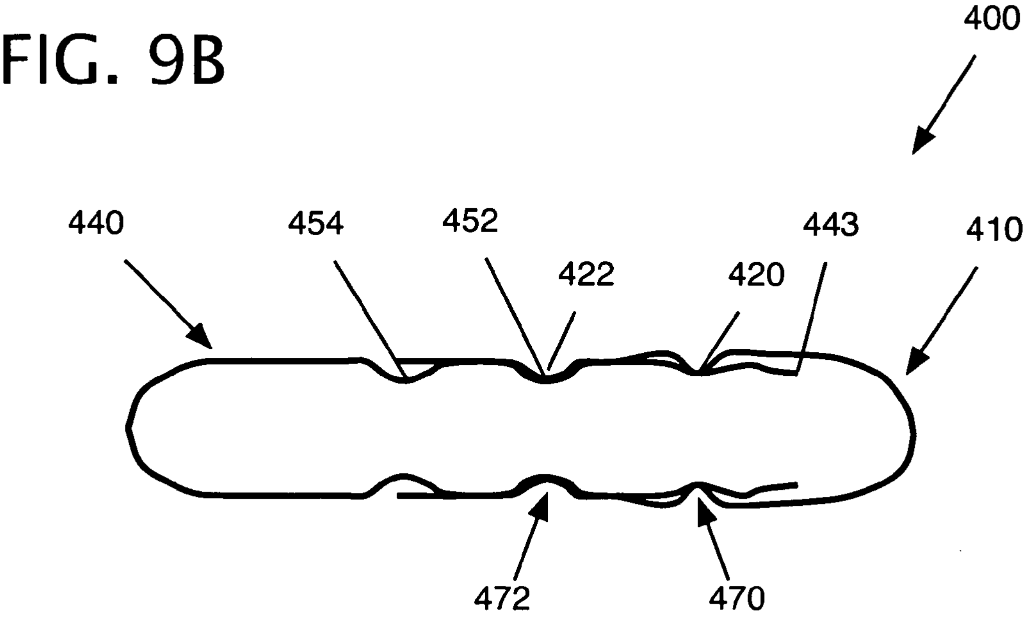

FIGS. 9A-B show cross-sectional side views of a capsule 400 according to another alternative embodiment of the invention. Here, body 440 contains only two channels 452, 454. As compared to the embodiment in FIGS. 8A-B, the first channel 350 (FIGS. 8A-B) has been removed. As such, in the prelock position of FIG. 9A, second channel 422 of cap 410 rests not within a channel, as in the embodiments described above, but adjacent a portion of body 440 between channel 452 and the inner taper 443 of the open end of body 440. As can be seen in FIG. 9A, open ends of cap 410 and/or body 440 may be deflected due to frictional contact in the prelock position. The degree of such deflection will depend, in part, upon the rigidities of cap 410 and body 440 and the degree of frictional contact therebetween.

In a prelock position, an interference between second channel 422 of cap 410 and body 440 is between about 5 μm and about 80 μm, preferably between about 0 μm and 30 μm, and most preferably about 19 μm. Accordingly, a force required to remove cap 410 from body 440, when in a prelock position such as that shown in FIG. 9A, is preferably between about 5 grams and about 55 grams, preferably between about 5 grams and about 40 grams, and most preferably between about 10 grams and about 30 grams (as an average from a measurement of 10 parts).

In a closed position, as shown in FIG. 9B, second channel 422 of cap 410 rests within channel 452 of body 440, forming fluid stop joint 472, as in the embodiments described above. However, unlike the embodiments above, snap fit joint 470 is formed by channel 420 of cap 410 deflecting and being deflected by a portion of body 440 between first channel 452 and inward taper 443. The degree of such deflection will depend, in part, upon the rigidities of cap 410 and body 440 and the amount of frictional contact therebetween. However, in general, less force is required to remove cap 410 from body 440 in the closed position of FIG. 9B than in the embodiments described above. Snap fit joint 470 includes an interference between cap 410 and body 440 of between about −20 μm and about 80 μm, and more preferably about 40 μm.

Figure 10A:
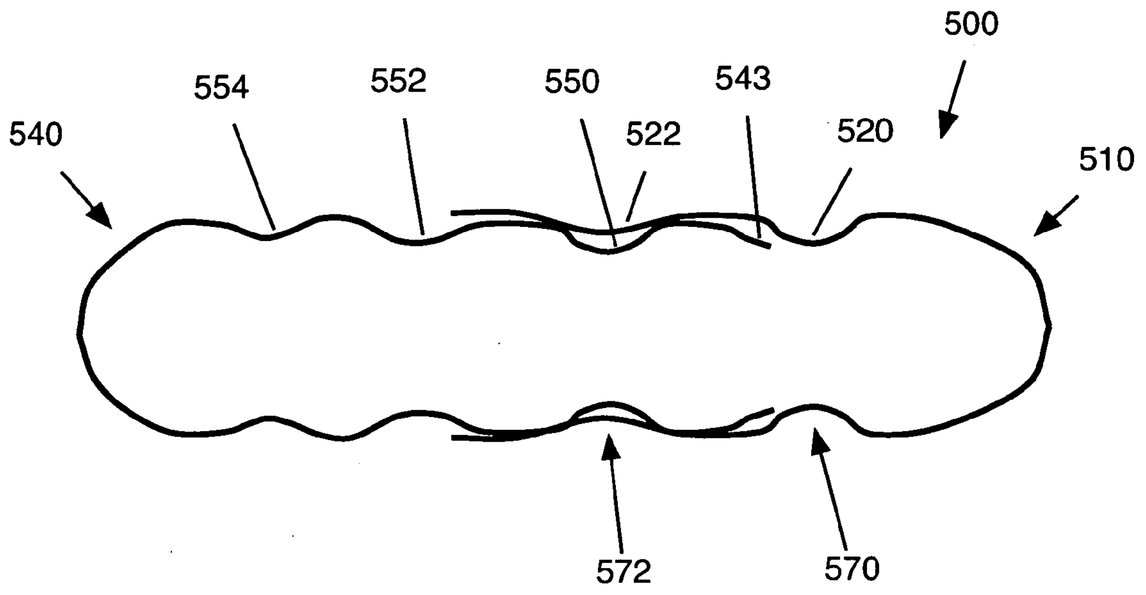
FIGS. 10A-B show cross-sectional side views of an alternative embodiment of the invention in prelock and closed positions, respectively.
Figure 10B:
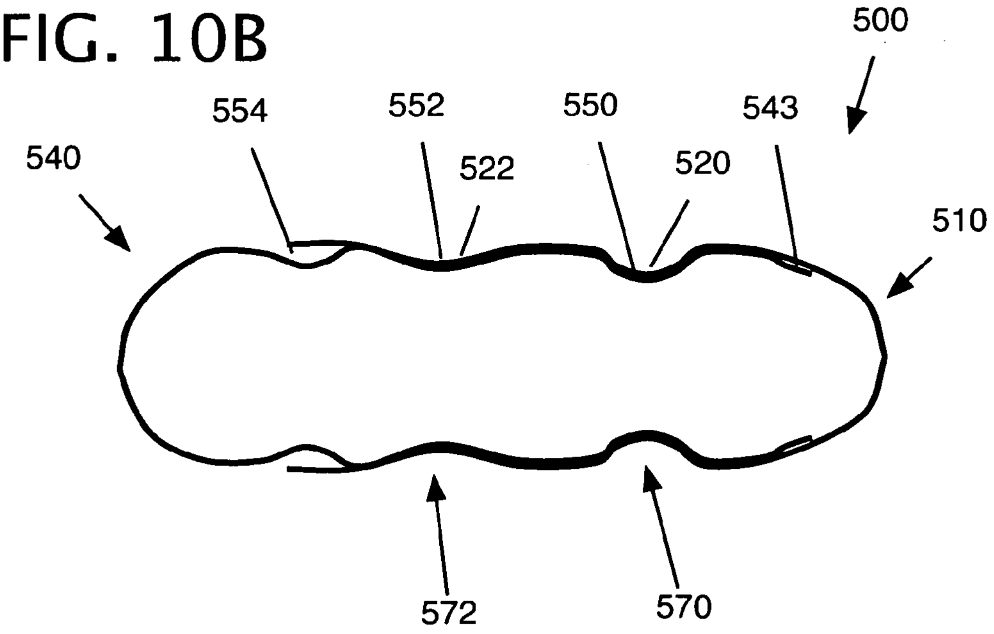

Referring now to FIGS. 10A-B, cross-sectional side views of yet another alternative embodiment of a capsule 500 according to the invention are shown. As in the embodiment shown in FIGS. 8A-B, body 540 includes three channels: first channel 550, second channel 552, and third channel 554. However, second channel 552 of body 540 is both higher and shallower than first channel 550 of body 540. Similarly, second channel 522 of cap is both higher and shallower than first channel 520 of cap 510 and, more importantly, is both higher and shallower than first channel 550 of body 540. As a result, in the prelock position shown in FIG. 10A, second channel 522 of cap 510 does not rest within first channel 550 of body 540. This results in a looser connection between cap 510 and body 540 in a prelock position. More particularly, in a prelock position, there is an interference between second channel 522 of cap 510 and body 540 of between about 5 μm and about 80 μm, preferably between about 0 μm and 30 μm, and most preferably about 19 μm Accordingly, a force required to remove cap 510 from body 540, when in a prelock position such as that shown in FIG. 10A, is preferably between about 5 grams and about 55 grams, preferably between about 5 grams and about 40 grams, and most preferably between about 10 grams and about 30 grams (as an average from a measurement of 10 parts).

FIG. 10B shows capsule 500 in a closed position. As noted above, first channel 520 of cap 510 and first channel 550 of body 540 are similar in shape, as are second channel 522 of cap 510 and second channel 552 of body 540. Thus, snap fit joint 570 and fluid stop joint 572 are formed as in the embodiments of FIGS. 2, 4, 5, 7, and 8A-B, with correspondingly-shaped channels in the cap and body and unlike the embodiment of FIGS. 9A-B. As a consequence, the force required to remove cap 510 from body 540 in the closed position of FIG. 10B is higher than in the embodiment of FIG. 9B.

Figure 11A:
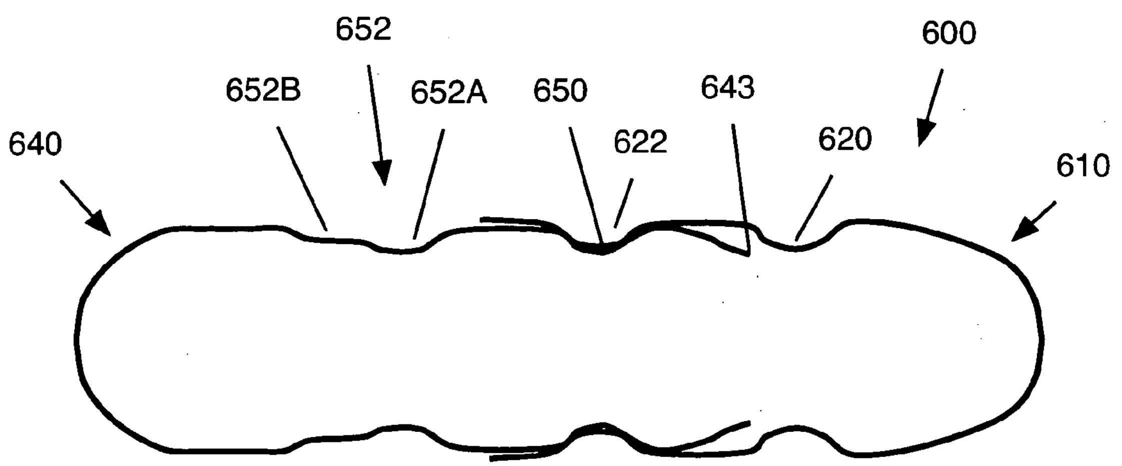
FIGS. 11A-B show cross-sectional side views of an alternative embodiment of the invention in prelock and closed positions, respectively.
Figure 11B:
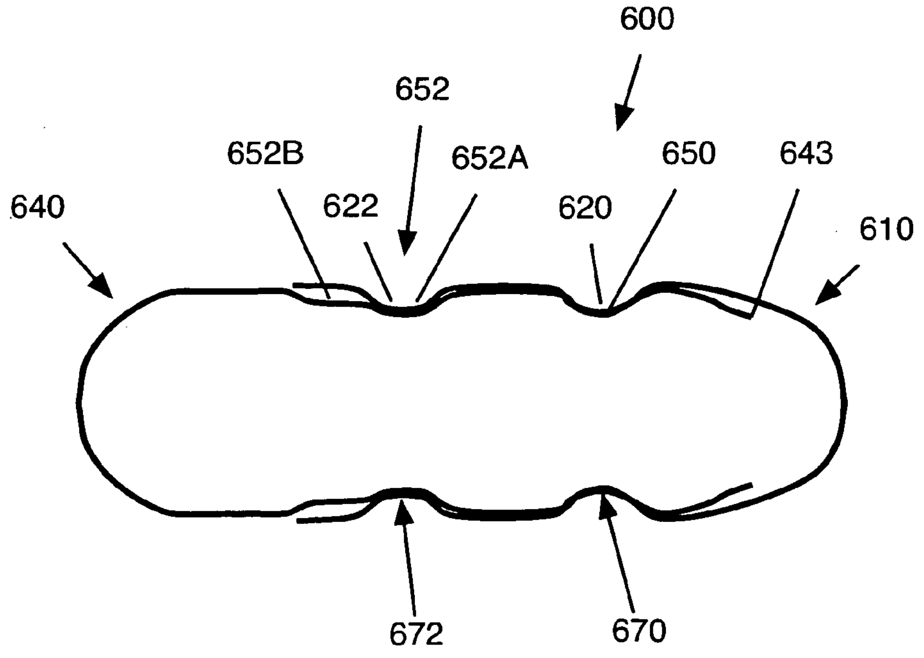

FIGS. 11A-B show cross-sectional side views of yet another alternative embodiment of a capsule 600 according to the invention. Body 640 includes two channels: first channel 650 and second channel 652. However, unlike other embodiments described above, second channel 652 includes a first portion 652A having a first depth and a second portion 652B having a second depth less than the first depth. First portion 652A is located closer to an open end of body 640 than is second portion 652B.

FIG. 11A shows capsule 600 in a prelock position, wherein second channel 622 of cap 610 rests within first channel 650 of body 640. FIG. 11B shows capsule 600 in a closed position, wherein first channel 620 of cap 610 rests within first channel 650 of body 640, forming snap fit ring 670, and second channel 622 of cap 610 rests within second channel 652 of body 640, forming fluid stop ring 672. More specifically, second channel 622 of cap 610 rests within first portion 652A of second channel 652 of body 640. In such an arrangement, second portion 652B provides a void beneath an open end of cap 610, into which a quantity of sealing fluid (not shown) may be contained. Capsule 600 is, therefore, particularly advantageous in ensuring adequate sealing of capsule 600 using a sealing fluid.

In known capsules, variations in cross-sectional shape and/or thicknesses of the cap and/or body walls can result in the cap and body touching at areas adjacent an open end of the cap, thereby preventing the entry of sealing fluid beneath the cap and providing a thorough seal. By including second portion 652B, an adequate seal is ensured by the provision of a void beneath an open end of cap 610 into which the sealing fluid may enter.

It should be recognized that the arrangement of first and second channels on one or both of a cap and body may be applied to any number of capsule arrangements. For example, U.S. Pat. No. 4,893,721 to Bodenmann et al., which is hereby incorporated by reference, describes a tamperproof capsule having a cap and a body of approximately the same length, the diameter of each being substantially less than its length.

Figure 12A:
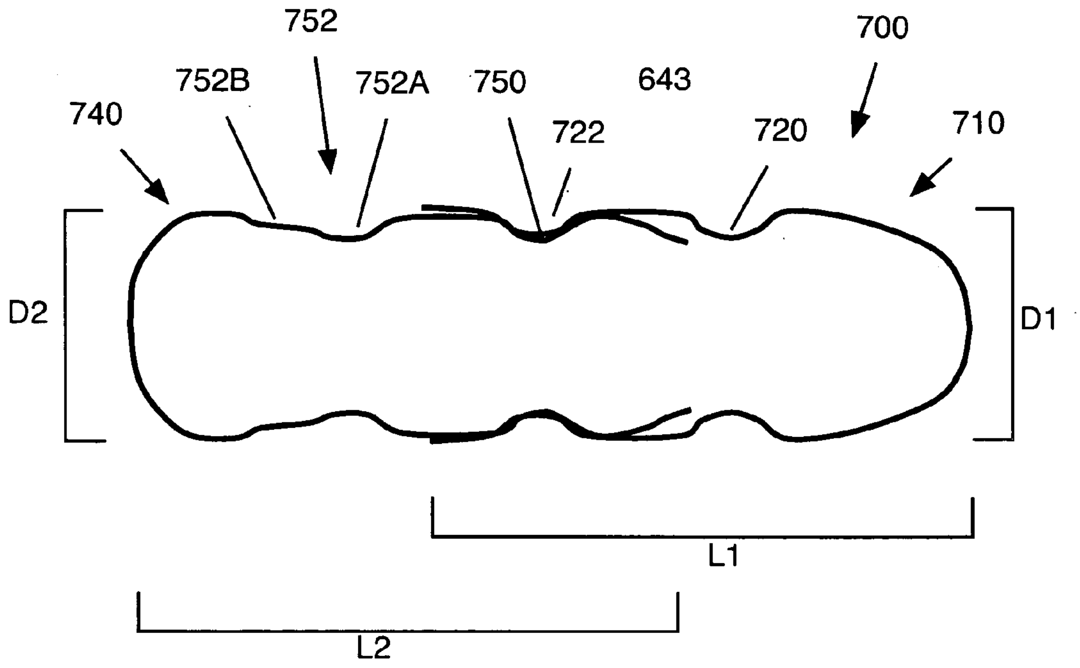
FIGS. 12A-B show cross-sectional side views of an alternative embodiment of the invention in prelock and closed positions, respectively.
Figure 12B:
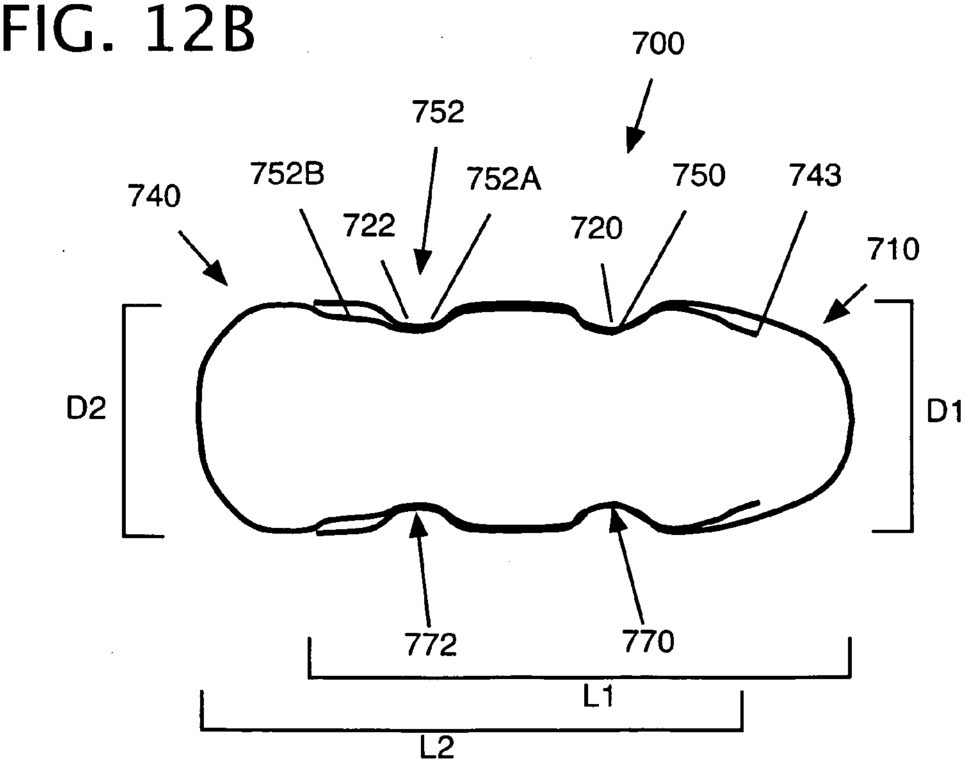

FIGS. 12A-B show a capsule 700 according to such an embodiment. In FIG. 12A, cap 710 and body 740 are shown in a prelock position. Cap 710 has a length L1 approximately equal to a length L2 of body 740. Similarly, each of L1 and L2 is greater than the diameters of cap 710, D1, and body 740, D2. As described above, D2 is necessarily equal to or slightly less than D1. In FIG. 12B, cap 710 and body 740 of capsule 700 are shown in a closed position, wherein the similarities in length of L1 and L2 are more clearly observable.

In any of the embodiments of the invention, the cap and body may be comprised of any number of materials known in the art including, for example, gelatin, hydroxypropylmethylcellulose, polyvinyl alcohol, hydroxypropyl starch, and pullulan. Pullulan is a particularly preferred material. The cap and body may each be comprised of more than one material and may each be of different materials or combinations of materials.

As noted above, the cap and the body may be further sealed using a sealing fluid 290 (FIGS. 2-5B) capable of at least partially dissolving and/or disintegrating a portion of the cap and/or body. Preferably, such dissolving and/or disintegrating occurs in an area between the cap and body, most preferably in an area adjacent an open end 212 (FIG. 2) of the cap. Any sealing fluid known in the art may be used, based upon the composition of the cap and body. Where the cap and/or body includes pullulan, a preferred sealing fluid contains at least one of water and an alcohol. A particularly preferred sealing fluid contains water and ethanol. As described below with respect to FIG. 13, excess sealing fluid may be removed by evaporation or suction.

Figure 13:
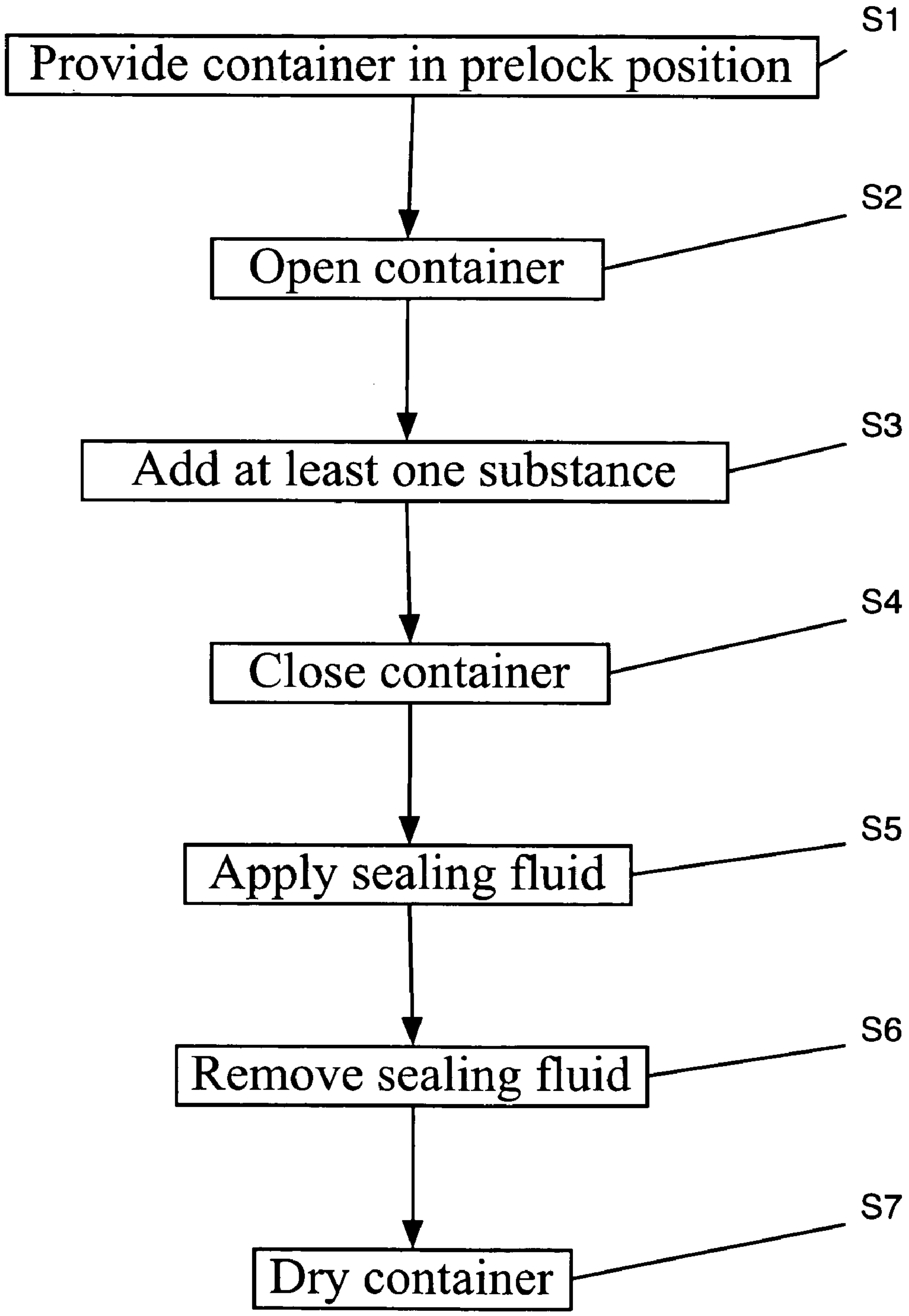
FIG. 13 shows a flow diagram of a method of filling and sealing a container of the invention.

Referring now to FIG. 13, a flow diagram is shown of a method of filling and sealing a container of the present invention. At step S1, a container according to one embodiment of the present invention is provided in a prelock position, such as that shown in FIGS. 7, 8A, 9A, 10A, 11A, and 12A. The container may be of any number of shapes and configurations, including those of the embodiments described above.

At step S2, the container is opened such that cap 210 (FIG. 7) and body 240 (FIG. 7) are not in contact. Once opened, a substance may be added to either or both of cap 210 (FIG. 7) and body 240 (FIG. 7) at step S3. The container of the present invention may be used to contain any number of substances to be delivered to an individual, including, for example, a pharmaceutical, a medicine, or a vitamin. The substance may take one or more of a number of forms, including, for example, a powder, a liquid, or a solid. Preferably, the substance is added only to body 240 (FIG. 7).

At step S4, the container is closed, whereby body 240 is inserted into cap 210, as shown, for example, in FIG. 2. At step S5, a sealing fluid 290 (FIG. 2) is applied to fluid gap 260 (FIG. 2) between the body and the cap. Sealing fluid at least partially dissolves and/or disintegrates at least one of the cap and the body. At step S6, excess sealing fluid is optionally removed. Such removal may be accomplished, for example, by the application of a suction force to the container. Finally, at step S7, the container is dried to substantially remove any remaining sealing fluid and fuse the at least partially dissolved and/or disintegrated portions of the cap and the body. The drying step may include, for example, heating the container. When heating is employed in the drying step, the container is preferably heated to between about 35° C. and about 55° C.

It should be noted, of course, that a container of the present invention may be provided in an open rather than a prelock position. As such, step S2 is unnecessary. Similarly, a container of the present invention may be provided in a closed position with a substance already contained therein. As such, steps S2 through S4 are unnecessary.

While this invention has been described in conjunction with the specific embodiments outlined above, it is evident that many alternatives, modifications and variations will be apparent to those skilled in the art. Accordingly, the embodiments of the invention as set forth above are intended to be illustrative, not limiting. Various changes may be made without departing from the spirit and scope of the invention as defined in the following claims.

What is claimed is:

1. A container comprising:

a cap;

a body slidably engagable inside the cap; and a fluid gap positioned between the cap and the body adjacent an end of the cap, wherein a first channel of the cap and a first channel of the body form a snap fit joint and a second channel of the cap and a second channel of the body form a fluid stop joint for preventing excess sealing fluid from entering into the fluid gap past the fluid stop joint.

2. The container of claim 1, wherein the first channel of the body and the second channel of the cap form a pre-lock joint.

3. The container of claim 2, wherein a force required to remove the cap from the body is between about 5 grams and about 55 grams.

4. The container of claim 2, wherein a height of the first channel of the body is greater than a height of the second channel of the cap.

5. The container of claim 2, wherein a depth of the first channel of the body is less than a depth of the second channel of the cap.

6. The container of claim 1, wherein a height of the second channel of the body is greater than a height of the first channel of the body.

7. The container of claim 6, wherein a height of the second channel of the cap is greater than a height of the first channel of the cap.

8. The container of claim 7, wherein the second channel of the cap and the first channel of the body form a pre-lock joint.

9. The container of claim 1, wherein a height of the second channel of the body is greater than a height of the second channel of the cap.

10. The container of claim 9, wherein a depth of at least a portion of the second channel of the body is greater than a depth of the second channel of the cap.

11. The container of claim 10, wherein the second channel of the body includes a first portion having a first depth and a second portion having a second depth, the first depth being greater than the second depth.

12. The container of claim 11, wherein the first portion is located closer to a closed end of the body than is the second portion.

13. The container of claim 1, further comprising a pressure release channel on a surface of the body and located substantially within an area of the snap fit joint.

14. The container of claim 1, further comprising at least one pillar on at least one of the following: an interior surface of the cap and an exterior surface of the body, the at least one pillar configured to reduce an amount of the sealing fluid at the end of the cap.

15. The container of claim 14, further comprising one of a gap and an interference between the at least one pillar and an exterior surface of the body of between a gap of about 5 μm and an interference of about 30 μm.

16. The container of claim 14, wherein the at least one pillar comprises a plurality of pillars forming a plurality of capillary channels between the interior surface of the cap and the exterior surface of the body.

17. The container of claim 16, wherein the plurality of pillars are evenly spaced circumferentially around the inner surface of the cap.

18. The container of claim 1, wherein the container includes at least one of the following: gelatin, hydroxypropylmethylcellulose, polyvinyl alcohol, hydroxypropyl starch, and pullulan.

19. The container of claim 1, wherein the body further comprises a third channel forming an entry gap adjacent the end of the cap.

20. The container of claim 1, wherein the first channel of the body is adjacent an open end of the body.

21. A container comprising:

a cap having a first channel and a second channel;

a body slidably engagable inside the cap, the body having a first channel engagable with the first channel of the cap in a first position and the second channel of the cap in a second position, a second channel engagable with the second channel of the cap in the first position, and a third channel forming an entry gap adjacent an open end of the cap; and a fluid gap between the cap and the body adjacent an end of the cap, wherein the first channels of the cap and the body form a snap fit joint and the second channels of the cap and the body form a fluid stop joint, whereby a sealing fluid is prevented from entering the fluid gap past the fluid stop joint.

22. The container of claim 21, wherein the first channel of the body is adjacent an open end of the body.

23. A container comprising:

a cap having a first channel and a second channel;

a body slidably engagable inside the cap, the body having a first channel engagable with the second channel of the cap and a second channel forming an entry gap adjacent an open end of the cap; and a fluid gap between the cap and the body adjacent an end of the cap, wherein the second channel of the cap and a portion of the body between an open end of the body and the first channel of the body form a pre-lock joint in a first position and the second channel of the cap and the first channel of the body form a fluid stop joint for preventing excess sealing fluid from entering into the fluid gap past the fluid stop joint in a second position.

24. The container of claim 23, wherein the container includes at least one of the following: gelatin, hydroxypropylmethylcellulose, polyvinyl alcohol, hydroxypropyl starch, and pullulan.

25. The container of claim 23, wherein the first channel of the cap and the portion of the body between the open end of the body and the first channel of the body form a snap fit joint in the second position.

26. A container comprising:

a cap;

a body slidably engagable inside the cap; and a fluid gap positioned between the cap and the body adjacent an end of the cap, wherein a first channel of the cap and a first channel of the body form a snap fit joint and a second channel of the cap and a second channel of the body form a fluid stop joint for preventing excess sealing fluid from entering into the fluid gap past the fluid stop joint, and wherein a length of the cap is substantially the same as a length of the body and greater than a diameter of either the cap or the body.

27. The container of claim 26, wherein the first channel of the body and the second channel of the cap form a pre-lock joint.

28. The container of claim 27, wherein a force required to remove the cap from the body is between about 5 grams and about 55 grams.

29. The container of claim 26, further comprising at least one pillar on at least one of the following: an interior surface of the cap and an exterior surface of the body, the at least one pillar configured to reduce an amount of the sealing fluid at the end of the cap.

30. The container of claim 29, wherein the at least one pillar comprises a plurality of pillars forming a plurality of capillary channels between the interior surface of the cap and the exterior surface of the body.

31. The container of claim 30, wherein the plurality of pillars are evenly spaced circumferentially around the inner surface of the cap.

32. The container of claim 26, wherein the container includes at least one of the following: gelatin, hydroxypropylmethylcellulose, polyvinyl alcohol, hydroxypropyl starch, and pullulan.

33. The container of claim 26, wherein the body further comprises a third channel forming an entry gap adjacent the end of the cap.

34. The container of claim 26, wherein the first channel of the body is adjacent an open end of the body.

* * * * *

UNITED STATES PATENT AND TRADEMARK OFFICE

CERTIFICATE OF CORRECTION

PATENT NO. : 8,377,471 B2
APPLICATION NO. : 11/498402
DATED : February 19, 2013
INVENTOR(S) : Vanquickenborne et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1672 days.

Signed and Sealed this
Ninth Day of December, 2014

Michelle K. Lee
*Deputy Director of the United States Patent and Trademark Office*